(12) United States Patent
Umeda et al.

(10) Patent No.: US 7,781,184 B2
(45) Date of Patent: Aug. 24, 2010

(54) METHOD OF ASSAYING SUBSTANCE CAPABLE OF CHANGING MITOCHONDRIAL MEMBRANE POTENTIAL

(75) Inventors: Asami Umeda, Tokyo (JP); Sumiko Nagaki, Tokyo (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 673 days.

(21) Appl. No.: 11/597,275

(22) PCT Filed: May 18, 2005

(86) PCT No.: PCT/JP2005/009066

§ 371 (c)(1),
(2), (4) Date: Jan. 22, 2007

(87) PCT Pub. No.: WO2005/111228

PCT Pub. Date: Nov. 24, 2005

(65) Prior Publication Data

US 2007/0202486 A1 Aug. 30, 2007

(30) Foreign Application Priority Data

May 18, 2004 (JP) .............................. 2004-147418

(51) Int. Cl.
*C12Q 1/00* (2006.01)
*C12Q 1/02* (2006.01)
(52) U.S. Cl. ........................................... 435/29; 435/4
(58) Field of Classification Search ........................ None
See application file for complete search history.

(56) References Cited

U.S. PATENT DOCUMENTS 5,169,788 A * 12/1992 Chen et al. .................. 436/172

7,160,687 B1 * 1/2007 Kapur et al. ................. 435/7.2

FOREIGN PATENT DOCUMENTS

| WO | WO 00/19200 | 4/2000 |
|---|---|---|
| WO | WO 00/68686 | 11/2000 |
| WO | WO 00/79274 | 12/2000 |

OTHER PUBLICATIONS

Ishida, Hideyuki et al., "Nicorandil attenuates the mitochondrial Ca$^{2}$+ overload with accompanying depolarization of the mitochondrial membrane in the heart", Naunyn-Schmiedeberg's Arch Pharmacol, vol. 369, No. 2, pp. 192-197, 2004.
Sato, Toshiaki et al., "Amiodarone Inhibits Sarcolemmal but Not Mitochondrial K$_{ATP}$ Channels in Guinea Pig Ventricular Cells", The Journal of Pharmacology and Experimental Therapeutics, vol. 307, No. 3, pp. 955-960, 2003.
Ishida, Hideyuki et al., "Opening of Mitochondrial KATP Channels Attenuates the Ouabain-Induced Calcium Overload in Mitochondria", Circulation Research, Journal of American Heart Association, vol. 89, pp. 856-858, 2001.
Minners, Jan et al., Ischemic and Pharmacological Preconditioning in Girardi Cells and C2C12 Myotubes Induce Mitochondrial Uncoupling , Circulation Research, Journal of The American Heart Association, vol. 89, No. 9, pp. 787-792, 2001.

* cited by examiner

*Primary Examiner*—Vera Afremova
(74) *Attorney, Agent, or Firm*—Oblon, Spivak, McClelland, Maier & Neustadt, L.L.P.

(57) ABSTRACT

The present invention aims to provide a convenient and high precision evaluation method of a pharmaceutical agent that changes the mitochondrial membrane potential, using a mitochondrial membrane potential of a cultured cell as an index.

The present invention provides a method for evaluating the ability of a test substance to change the mitochondrial membrane potential by using, as an index, the change in the mitochondrial membrane potential, which is produced by the addition of an ion permeability regulator on a cellular membrane to a cell culture medium, wherein the change is measured as variation in the fluorescent intensity of a fluorescent dye.

12 Claims, 3 Drawing Sheets

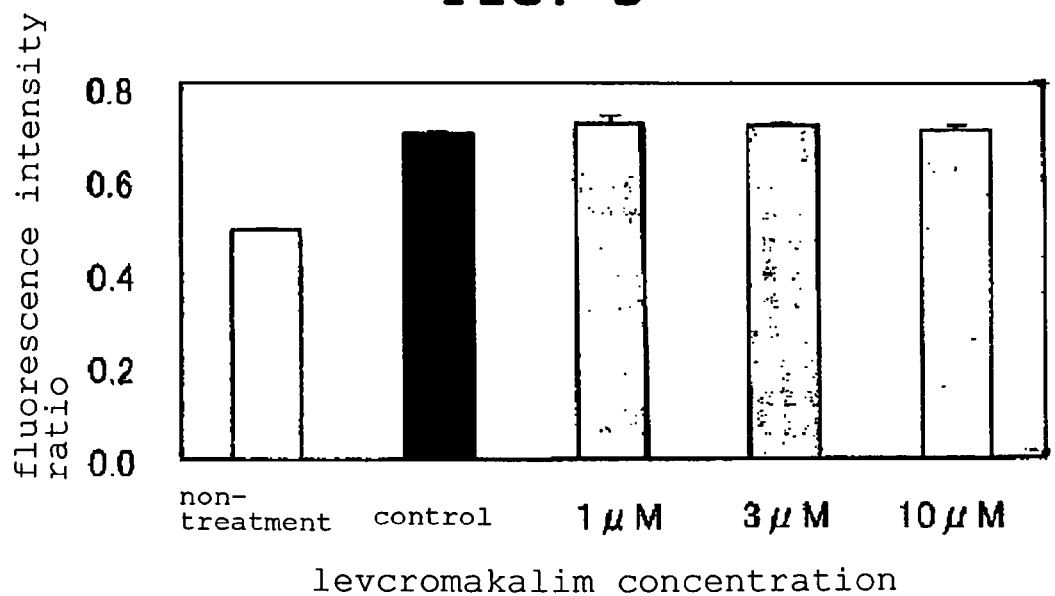
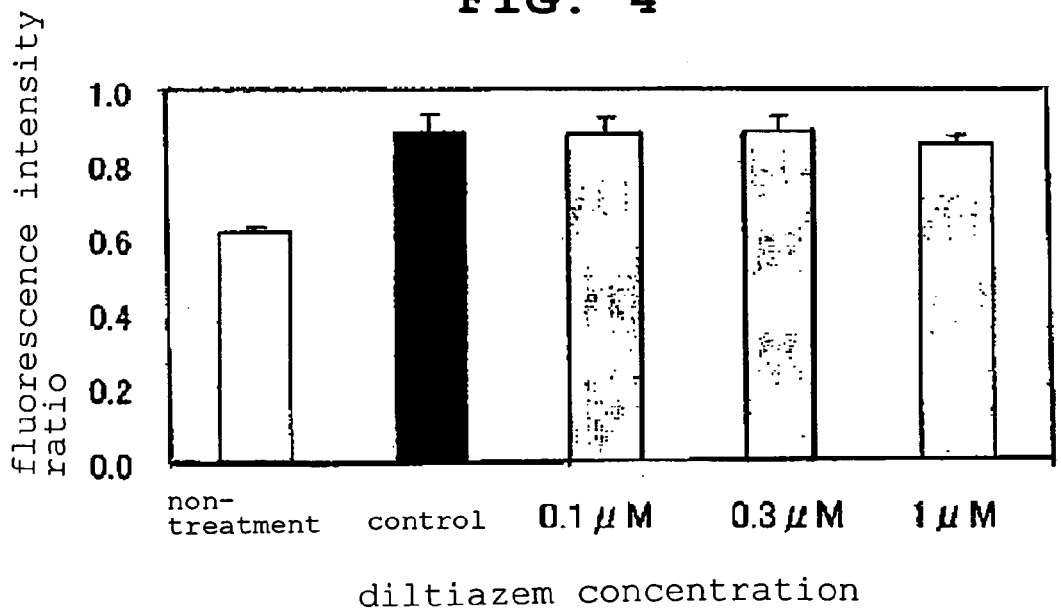

METHOD OF ASSAYING SUBSTANCE CAPABLE OF CHANGING MITOCHONDRIAL MEMBRANE POTENTIAL

TECHNICAL FIELD

The present invention relates to an evaluation method of a substance capable of changing the mitochondrial membrane potential. Alternatively, it relates to an evaluation method of a substance inhibiting calcium influx into mitochondria.

More particularly, the present invention relates to an evaluation method of an ATP-sensitive $K^+$ channel (mitochondrial ATP-sensitive $K^+$ channel, hereinafter to be referred to as mito $K_{ATP}$ channel) opener in the inner mitochondrial membrane.

BACKGROUND ART

Cellular membrane ATP-sensitive K+ channel (hereinafter to be referred to as sarc$K_{ATP}$ channel) is known to present in the myocardium cellular membrane, smooth muscle cellular membrane and pancreatic β cell membrane, and regulate the calcium concentration in the cytoplasm (see non-patent reference 1). Conventionally, openers of the $K_{ATP}$ channel in the myocardium cellular membrane and smooth muscle cellular membrane have been studied as therapeutic drugs for angina pectoris and hypertension. The $K_{ATP}$ channel blocker of the pancreatic β cellular membrane has been placed in the market as a therapeutic drug for diabetes.

In recent years, it has been pharmacologically and physiologically shown that the mito$K_{ATP}$ channel is present and ischemic injury of cell can be prevented by opening the channel (see non-patent reference 2).

During ischemia, in the cell, Na/K ATPase activity on the cellular membrane decreases due to the cessation of energy production, and intracellular Na concentration increases. Upon reperfusion of blood flow, intracellular Na that increased during ischemia is exchanged with extracellular Ca to increase intracellular Ca. Ca influx into mitochondria increases intramitochondrial Ca concentration and depolarizes inner mitochondrial membrane. Moreover, the reactive oxygen species produced by reperfusion also promotes depolarization of the inner mitochondrial membrane.

When the mito$K_{ATP}$ channel is previously opened, Ca influx into mitochondria can be inhibited during reperfusion, and depolarization of the inner mitochondrial membrane is also inhibited (see non-patent reference 3).

For study of the relationship between the mito$K_{ATP}$ channel opening action and pathology, (1) an evaluation method using a cell line such as Girardi cell, PC12 cell, SHSY-5Y cell, human neuroblastoma cell, primary cultured rat cardiac muscle cell and the like, (2) an evaluation method using mitochondria isolated from a cell by centrifugation, (3) a method based on the evaluation of the effect on the isolated heart and the like are generally known.

Furthermore, the following evaluation method using Griardi cells (GIRARDI HEART: ECACC No. 9312082) has been reported.

(1) Griardi cells were seeded on a 24-well culture plate, adenosine or diazoxide (mito$K_{ATP}$ channel opener) was added, the cells were cultured for 3 hr in an acidified culture medium containing a metabolism inhibitor and the like under low oxygen conditions to reproduce an ischemic state, and further cultured for 1 hr in a normal culture medium at a normal oxygen concentration. Thereafter, to evaluate the level of apoptosis, a cell death indicator PI (propidium iodide) was added, and the cells were treated with trypsin and EDTA to be floated. The fluorescence at 565-640 nm emitted by the dead cells that had incorporated PI was measured by flow cytometry, and the cell number distribution was determined. In addition, without treating the cells with PI and trypsin, the concentration of lactic acid dehydrogenase in the culture supernatant was measured. As a result, adenosine strongly inhibited apoptosis, and the effect was clarified to have derived from a mito$K_{ATP}$ channel opening action via activation of the p38MAP kinase system (see non-patent reference 4).

Alternatively, (2) Griardi cells were seeded on a 6- or 24-well culture plate, cultured for a given time in a culture medium containing mitochondrial membrane potential sensitive dye JC-1, and then in a culture medium containing a mitochondrial depolarizing agent CCCP, and the change in the intensity of red fluorescence, which is an index of the mitochondrial membrane potential, was examined by flow cytometry. As a result, decreased fluorescence intensity and depolarization of mitochondria were observed (see non-patent reference 5).

Meanwhile, there is a report confirming a mito$K_{ATP}$ channel opening action of diazoxide in primary cultured rat neonatal cardiac muscle cell, utilizing the properties of ouabain, a cellular membrane Na/K ATPase inhibitor, to increase the intracellular Ca concentration and intramitochondrial Ca concentration (see non-patent reference 6).

However, the conventional methods are associated with aspects yet to be improved.

To be specific, in the aforementioned methods, (1) during cultivation under low oxygen conditions, the culture environment is difficult to maintain at a constant level and the levels of injury easily vary among wells; (2) cells need to be prepared in large amounts since cell injury is determined by flow cytometry or lactic acid dehydrogenase concentration measurement; (3) in flow cytometry, the operation up to a fluorescence detection is complicated; and (4) in the measurement of lactic acid dehydrogenase concentration, the measurement of absorbance is complicated.

On the other hand, a screening method of a compound influential on the oxidization-reduction potential of mitochondria, which is based on the measurement of the fluorescence change, has been reported (patent reference 1). Nevertheless, even by the method described in patent reference 1, evaluation of one sample requires a complicated operation and a considerable amount of operation time.

As described above, since conventional methods have difficulty in reproducing constant conditions, and since the time and labor necessary for the evaluation are enormous, the methods are not suitable for a simultaneous evaluation of a large number of pharmaceutical agents. patent reference 1: WO99/53024
non-patent reference 1: Kidney Int. 57, 838, 2000
non-patent reference 2: Circ Res. 84, 973, 1999
non-patent reference 3: Cardiovasc. Res. 55, 534, 2002
non-patent reference 4: Basic Res. Cardiol. 95, 243, 2000
non-patent reference 5: Cardiavasc. Res. 51, 691, 2001
non-patent reference 6: Circ. Res. 89, 856, 2001

DISCLOSURE OF THE INVENTION

Problems to be Solved by the Invention

The present invention aims to provide a convenient and high precision evaluation method of a pharmaceutical agent that changes the mitochondrial membrane potential, using the mitochondrial membrane potential of a cultured cell as an index.

Means of Solving the Problems

The present inventors cultured Girardi cells, stained mitochondria with mitochondrial membrane potential sensitive dye JC-1, determined the intensity ratio of JC-1 monomer fluorescence and J-aggregate fluorescence (monomer/J-aggregate), developed by the excitation light, by a fluorescence plate reader, and measured the mitochondrial membrane potential with the fluorescence intensity ratio as an index. As a result, they have found that a concurrent addition of KCl to ouabain results in a mitochondrial depolarization in a short time with good reproducibility. Furthermore, they have found that the addition of a test substance to the test system enables evaluation of mitochondrial depolarization-inhibiting activity, i.e., whether a test substance has an activity as a mitoK$_{ATP}$ channel opener, as well as the intensity of the activity, and have further conducted intensive studies, which resulted in the completion of the present invention.

Accordingly, the present invention relates to the evaluation methods of the following (1) to (27).

(1) The present invention provides an evaluation method of a substance that changes the mitochondrial membrane potential, which comprises adding a regulator of cellular membrane ion permeability. Since the mitochondrial membrane potential can change due to calcium influx into mitochondria, the present invention also encompasses an evaluation method of a substance inhibiting calcium influx into mitochondria.

(2) The present invention provides the evaluation method of the aforementioned (1), which comprises the following steps of:
(a) contacting a cultured cell with a test substance,
(b) contacting the cultured cell with a regulator of cellular membrane ion permeability, and
(c) measuring the change in a mitochondrial membrane potential of the cultured cell.

Therefore, the order of (a) and (b) does not matter in the present invention, where (a) may or may not precede (b) in the present invention, and (a) and (b) may be performed simultaneously.

(3) The present invention provides the evaluation method of the aforementioned (2), wherein the aforementioned (a) to (c) further comprise (d) selecting a test substance that changes the mitochondrial membrane potential of the cultured cell.

(4) The present invention provides the evaluation method of the aforementioned (3), wherein the substance in (d) inhibits cell apoptosis.

(5) The present invention provides the evaluation method of the aforementioned (3) or (4), wherein the substance in (d) inhibits calcium influx into mitochondria.

(6) The present invention provides the evaluation method of any one of the aforementioned (3) to (5), wherein the substance in (d) acts on the mitochondrial ATP-sensitive K$^+$ channel.

(7) The present invention provides the evaluation method of any one of the aforementioned (2) to (6), wherein the cultured cell has a high sensitivity to an ion permeability regulator of the cellular membrane.

(8) The present invention provides the evaluation method of the aforementioned (7), wherein the cultured cell has a high sensitivity to an Na/K ATPase inhibitor.

(9) The present invention provides the evaluation method of the aforementioned (8), wherein the cultured cell has a high sensitivity to ouabain.

(10) The present invention provides the evaluation method of any one of the aforementioned (2) to (9), wherein the cultured cell is a cell line.

(11) The present invention provides the evaluation method of the aforementioned (10), wherein the cultured cell is a human cell line.

(12) The present invention provides the evaluation method of the aforementioned (11), wherein the cultured cell is derived from human heart, brain, nerve, liver or pancreas.

(13) The present invention provides the evaluation method of the aforementioned (12), wherein the cultured cell is a Girardi cell.

(14) The present invention provides the evaluation method of any one of the aforementioned (2) to (13), wherein the cultured cell is cultured on a plate usable for an optical measurement method.

(15) The present invention provides the evaluation method of any one of the aforementioned (2) to (6), wherein the regulator of cellular membrane ion permeability induces the change in the mitochondrial membrane potential.

(16) The present invention provides the evaluation method of the aforementioned (15), wherein the regulator of cellular membrane ion permeability is an ion transporter regulator or ion permeable channel regulator of a cellular membrane.

(17) The present invention provides the evaluation method of the aforementioned (16), wherein the ion transporter regulator or ion permeable channel regulator is an Na$^+$/Ca$^{++}$ exchange system inhibitor, an Na$^+$/H$^+$ exchange system inhibitor, a Ca$^{++}$ modulator or an Na/K ATPase inhibitor.

(18) The present invention provides the evaluation method of the aforementioned (17), wherein the ion transporter regulator or ion permeable channel regulator is an Na/K ATPase inhibitor.

(19) The present invention provides the evaluation method of the aforementioned (18), wherein the Na/K ATPase inhibitor is ouabain.

(20) The present invention provides the evaluation method of any one of the aforementioned (2) to (6), wherein "(b) contacting the cultured cell with a regulator of cellular membrane ion permeability" is performed under a high potassium ion concentration.

(21) The present invention provides the evaluation method of the aforementioned (20), wherein the potassium ion concentration is 20-90 mM.

(22) The present invention provides the evaluation method of the aforementioned (20) or (21), wherein the regulator of cellular membrane ion permeability is ouabain.

(23) The present invention provides the evaluation method of the aforementioned (22), wherein ouabain has a concentration of 0.1 µM-3 mM.

(24) The present invention provides the evaluation method of any one of the aforementioned (1) to (6), wherein the change in the membrane potential is measured by the fluorescent color of a fluorescent dye incorporated into the cell.

(25) The present invention provides the evaluation method of the aforementioned (24), wherein the fluorescent dye develops two colors.

(26) The present invention provides the evaluation method of the aforementioned (25), wherein the change in the membrane potential is measured by the ratio of the two fluorescent colors.

(27) The present invention provides the evaluation method of any one of the aforementioned (24) to (26), wherein the fluorescent dye is JC-1.

Effect of the Invention

Using the evaluation method of the present invention, a pharmaceutical agent that selectively acts on the mitoK$_{ATP}$ channel can be evaluated.

Using the evaluation method of the present invention, a pharmaceutical agent that changes the mitochondrial membrane potential can be evaluated conveniently with high precision.

Using the evaluation method of the present invention, a pharmaceutical agent that changes the mitochondrial membrane potential can be evaluated in a short time.

BRIEF DESCRIPTION OF THE DRAWINGS

FIG. 3 shows the relationship between the concentration of levcromakalim and the fluorescence intensity ratio (Example 1).

FIG. 4 shows the relationship between the concentration of diltiazem and the fluorescence intensity ratio (Example 1).

BEST MODE FOR EMBODYING THE INVENTION

Figure 1:
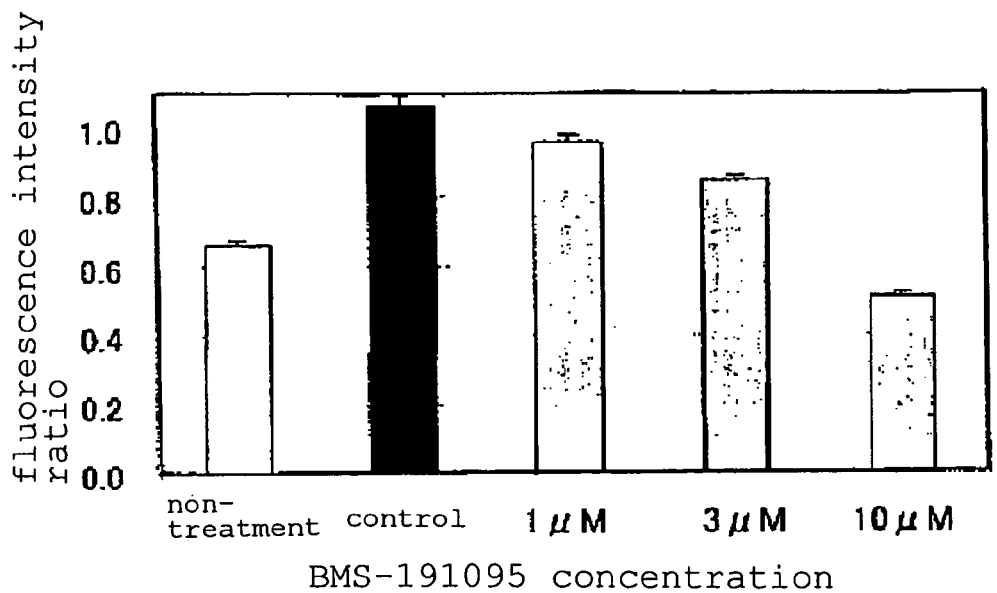
FIG. 1 shows the evaluation of the mitochondrial depolarization action of BMS-191095, wherein the concentration of BMS-191095 and difference in the fluorescence intensity ratio were used as indices (Example 1).
Figure 2:
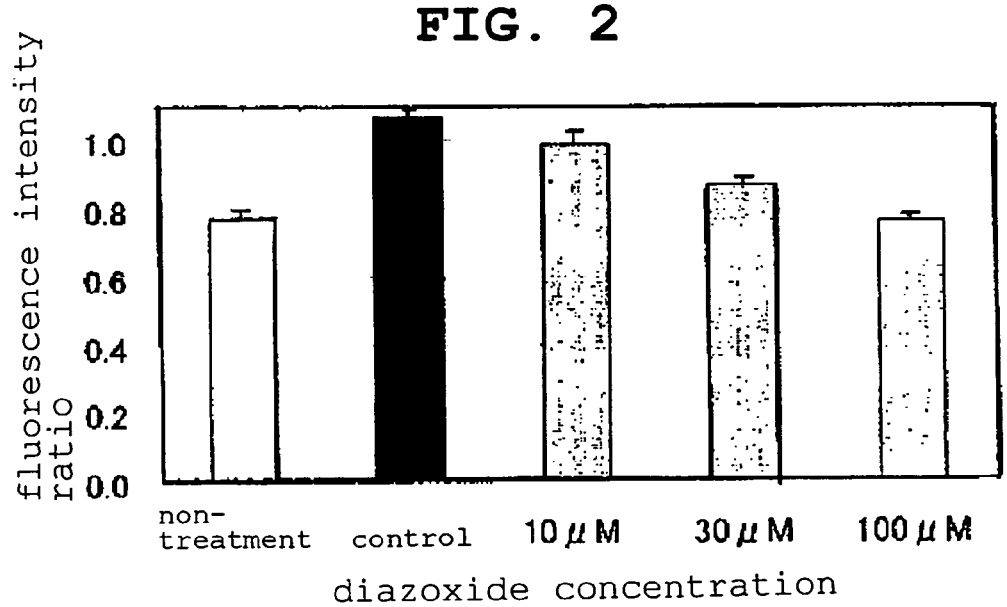
FIG. 2 shows the evaluation of the mitochondrial depolarization action of diazoxide, wherein the concentration of diazoxide and difference in the fluorescence intensity ratio were used as indices (Example 1).

In the present invention, the ability of a test substance to change the mitochondrial membrane potential is evaluated by using, as an index, the change in the mitochondrial membrane potential, which is produced by contacting an ion permeability regulator on a cellular membrane with a cultured cell, wherein the change is measured as a variation in the fluorescent intensity of a fluorescent dye. Furthermore, the present invention is preferably practiced under high potassium ion concentration conditions.

According to the present invention, a substance that changes the mitochondrial membrane potential can be selected, by which a substance capable of inhibiting cellular apoptosis, a substance capable of inhibiting calcium influx into mitochondria, and a substance capable of acting on the mitochondria ATP-sensitive K$^+$ channel can be selected.

The cultured cell to be used in the present invention is preferably a cultured cell having high sensitivity to a regulator of cellular membrane ion permeability, particularly an Na/K ATPase inhibitor, more preferably a cultured cell having high sensitivity to ouabain. The cell having "high sensitivity" means a cell showing a sufficient change in the membrane potential by the addition of an ion permeability regulator, an Na/K ATPase inhibitor or ouabain and, for example, a cell showing a significantly different fluorescence intensity ratio by the addition of an ion permeability regulator, an Na/K ATPase inhibitor or ouabain, as compared to culture conditions free of the addition.

The cultured cell to be used in the present invention means a cell line or a primary cultured cell. A preferable example thereof is a cell line, more preferably a human cell line. The "human cell line" means an established cell line derived from a human tissue, which has acquired an infinite proliferation ability. Of such human cell lines, one derived from a human organ or tissue such as the heart, brain, nerve, liver, pancreas and the like is more preferable.

The "Girardi cell" to be used in the present invention means a Girardi cell (GIRARDI HEART, ECACC No. 9312082) derived from human heart, which is available from the European Collection of Cell Culture.

The "test substance" to be used in the present invention is not particularly limited as long as it can be added to the evaluation system of the present invention and, for example, a cell extract, a cell culture supernatant, a fermentative microorganism product, a marine organism extract, a botanical extract, a purified or crudely-purified protein, a peptide, a non-peptidic compound, a nucleic acid, a synthesized low-molecular-weight compound, a natural compound, and the like can be mentioned.

The "regulator of cellular membrane ion permeability" to be used in the present invention means a substance influential on the ion permeability of the cellular membrane. Preferable specific examples of the regulator of cellular membrane ion permeability include an "ion transporter regulator", an "ion permeable channel regulator" and the like. Preferable specific examples of these regulators include Na$^+$/Ca$^{++}$ exchange system inhibitors (dichlorobenzamile etc.), Na$^+$/H$^+$ exchange system inhibitors (amiloride, cariporide etc.), Ca$^{++}$ channel modulators (nifedipine, nicardipine, diltiazem, verapamil, Bay K 8644, maitotoxin etc.), Na$^+$ channel modulators (tetrodotoxin, veratridine, batrachotoxin, monensin etc.), K+ channel modulators (5-hydroxydecanoic acid, HMR-1098, levcromakalim, pinacidil, 4-aminopyridine, tetraethylammonium, valinomycin etc.), Na/K ATPase inhibitors (ouabain, digoxin, digitoxin etc.), and the like. For example, the concentration when ouabain is used is preferably 0.1 μM-3 mM, more preferably 100 μM-2 mM.

The "contacting the cultured cell with a test substance" in the present invention is not particularly limited as long as the cultured cell can be brought into contact with a test substance and, for example, steps wherein a test substance is present in a cell culture medium, such as addition of a test substance to a cell culture medium under culture, cultivating cells in a cell culture medium adjusted in advance by the addition of a test substance and the like, and the like can be mentioned.

The "contacting the cultured cell with a regulator of cellular membrane ion permeability" in the present invention is not particularly limited as long as the cultured cell can be brought into contact with a regulator of cellular membrane ion permeability and, for example, addition of a regulator of cellular membrane ion permeability to a cell culture medium under culture, cultivating cells in a cell culture medium adjusted in advance by the addition of a regulator of cellular membrane ion permeability and the like, and the like can be mentioned.

As the mode of embodiment of the present invention, an embodiment wherein a cell culture medium containing a test substance and a cell culture medium containing a regulator of cellular membrane ion permeability are separately prepared, and these cell culture media are added to cells for cultivation thereof, an embodiment wherein a cell culture medium containing a test substance and a regulator of cellular membrane ion permeability is prepared, which is added to cells for cultivation thereof can be mentioned.

The "cell culture medium" to be used in the present invention is not particularly limited as long as the object cell can be cultured and any medium containing serum, serum-free medium, buffer and the like can be used.

The "high potassium ion concentration" in the present invention means a concentration higher than that of a potassium ion (5-10 mM) generally used for cell culture, and is preferably 20-90 mM. The method for adjusting potassium ion is exemplified by, but not limited to, addition of a given amount of KCl.

The "plate usable for an optical measurement method" in the present invention mainly refers to a 96-well clear bottom black plate or black plate. Besides these, as a cell culture plate measurable on a fluorescence plate reader, for example, 384-, 48-, 24-, 12- and 6-well plates and the like can be mentioned.

The "fluorescent dye" in the present invention means a fluorescent dye sensitive to a change in the mitochondrial membrane potential and, for example, JC-1 can be mentioned.

"JC-1" (sometimes to be referred to as "mitochondrial membrane potential sensitive dye JC-1") is 5,5',6,6'-tetrachloro-1,1',3,3'-tetraethylbenzimidazolcarbocyanine iodide (Molecular Probes T-3168). This compound is taken up into cell, migrated into mitochondria, and forms an aggregate called J-aggregate when mitochondria is normal and potential difference from the outside is around −180 mV. The aggregate emits red fluorescence having a peak at 590-600 nm by the excitation at 488-490 nm. On the other hand, JC-1 in the cytoplasm becomes a monomer emitting green fluorescence having a peak at 527 nm. When mitochondria is depolarized, JC-1 cannot form J-aggregate, and therefore, red fluorescence decreases and green fluorescence increases. Utilizing such property, the fluorescence intensity ratio of monomer/J-aggregate is detected to observe the mitochondrial membrane potential.

The outline of the evaluation method of the present invention is shown in the following.

First of all, Girardi cells are seeded on a plate usable for an optical measurement method, and cultured in a normal medium (MEM medium supplemented with additives, such as non-essential amino acid, fetal bovine serum and the like). Then, the medium is changed to a normal medium containing JC-1 to allow incorporation of JC-1 into the cell, the medium is changed to a normal medium containing a test substance, and the cells are cultured. Then, a depolarization-inducing medium is used (normal medium containing ouabain and KCl; in the evaluation method of the present invention, ouabain is used at a concentration of 0.1 µM-3 mM, and KCl is used at a concentration of 20 mM-90 mM). The test substance may be added along with or after addition of a depolarization-inducing medium following incorporation of JC-1 into the cell. After addition of the depolarization-inducing medium, the culture time can be 1-24 hr. Thereafter, the fluorescence of JC-1 monomer and the fluorescence of J-aggregate are measured on a fluorescence plate reader (capable of excitation at around 488-490 nm, which is the excitation wavelength of JC-1, and capable of fluorescence detection around 527 nm, which is the fluorescence wavelength peak of JC-1 monomer and around 590-600 nm, which is the fluorescence wavelength of J-aggregate), and the fluorescence intensity ratio (monomer fluorescence intensity/J-aggregate fluorescence intensity) is calculated.

The following 4 kinds of wells are set on the same plate, and the activity is calculated as shown in the following.
(1) non-treatment: well added with normal medium instead of depolarization-inducing medium,
(2) control: well free of test substance,
(3) test substance: well added with various kinds of test substances at each concentration,
(4) blank: well free of JC-1.

When the monomer fluorescence intensity and J-aggregate fluorescence intensity of the respective wells are shown as (1) m or (1) J, A: fluorescence intensity ratio of 'non-treatment'=[(1)m-(4)m]/[(1)J-(4)J]

B: fluorescence intensity ratio of 'control'=[(2)m-(4)m]/[(2)J-(4)J]

C: fluorescence intensity ratio of 'test substance'=[(3)m-(4)m]/[(3)J-(4)J], in which when B increases more than A and depolarization is confirmed, the mitoK$_{ATP}$ channel opening activity of the test substance is detected based on the degree of decrease of C as compared to B.

The present invention is explained in more detail in the following by referring to Examples, which are not to be construed as limitative.

EXAMPLE 1

The pharmaceutical agents (compounds) evaluated by the present evaluation method are as follows.

BMS-191095: synthesized according to J. Med. Chem., vol. 40, 24-34 (1997) and used for the experiment.

levcromakalim (GlaxoSmithKline): compound 2 described in J. Med. Chem., vol. 29, 2194-2201 (1986) was synthesized and used for the experiment.

diazoxide: SIGMA D9035 was purchased and used for the experiment.

diltiazem hydrochloride: SIGMA D2521 was purchased and used for the experiment.

Girardi cells suspended in a normal medium [(MEM (GIBCO 11095-098) supplemented with 1% non-essential amino acid (MEM Non-Essential Amino Acids Solution 10 mM 100× GIBCO 11140-050), and 10% fetal bovine serum (BIOFLUIDS DIVISION Lot No. 302030))] were seeded to a 96-well clear bottom black plate (MATRIX MT4940) at 200 µL/well and cultured.

JC-1 (Molecular Probes T-3168, 1 mg/mL DMSO solution) was added to a phenol red-free normal medium [MEM (GIBCO 51200-038) supplemented with 1% non-essential amino acid (MEM Non-Essential Amino Acids Solution 10 mM 100× GIBCO 11140-050), 1% L-glutamine (L-Glutamine-200 mM 100×: GIBCO 25030-149) and 10% fetal bovine serum (BIOFLUIDS DIVISION: Lot No. 302030)] at 10 µL/mL, the mixture was stirred with a vortex mixer and centrifuged at 3000 rpm for 1 min and the supernatant was filtered through a syringe filter (0.22 µm, MILLIPORE). The medium in the 96-well plate was removed and the JC-1 solution was dispensed to a cell-seeded well at 50 µL/well. A phenol red-free normal medium without JC-1 was dispensed to a blank well. The plate was placed back in a $CO_2$ incubator and incubated for 20 min.

Then, each well washed once with a phenol red-free normal medium (200 µL) and the same medium containing various concentrations of each test substance was dispensed at 50 µL/well. Each test substance was dissolved in DMSO (Dimethyl Sulfoxide: SIGMA D-8779) to the final DMSO concentration of 0.1%.

A medium containing 0.1% DMSO was dispensed to the wells of 'without treatment' and 'control' at 50 µL/well. The plate was placed back in a $CO_2$ incubator and incubated for 25 min.

Then, a depolarization-inducing medium containing 1 mM ouabain, 60 mM, and a test substance at each concentration (prepared from phenol red-free normal medium as a base) was dispensed to the well of 'test substance' by 50µL. A normal medium containing 0.1% DMSO was dispensed to the well of 'without treatment', and a depolarization-inducing medium containing 0.1% DMSO was dispensed to the well of 'control' by 50 µL/well.

The plate was placed back in a $CO_2$ incubator and incubated for 2 hr.

After induction of depolarization, the plate was set on a fluorescence plate reader (TECAN, SpectraFluor) heated to 37° C., and the J-aggregate fluorescence was measured at 595 nm using an excitation wavelength of 485 nm. Then, the monomer fluorescence was measured at 535 nm using an excitation wavelength of 485 nm. The measurement was performed at flash frequency of 20 times and 50 µsec intervals. Each group contained 4 wells. The average value of fluorescence intensity of the 'blank' well was subtracted from the value of each well of 'without treatment', 'control' and 'test substance' for each of monomer fluorescence and J-aggregate fluorescence, and the ratio of each fluorescence intensity, monomer/J-aggregate, was determined.

The results are shown in FIG. 1 to FIG. 4 (mean±standard error, N=4).

As a result of the experiment according to the evaluation method of the present invention, the mitochondrial depolarization inhibitory action could be conveniently evaluated for BMS-191095 (FIG. 1) and diazoxide (FIG. 2) confirmed by other evaluation methods to have a mitoK$_{ATP}$ channel open action.

In contrast, levcromakalim (FIG. 3), which is a sarcK$_{ATP}$ channel opener, and diltiazem (FIG. 4), which is a calcium antagonist, did not prevent mitochondrial depolarization.

From the above, it is appreciated that the evaluation method of the present invention can specifically detect a mitoK$_{ATP}$ channel opener by a convenient operation as compared to conventional evaluation methods.

EXAMPLE 2

Girardi cells were suspended in a normal medium [(MEM (GIBCO 11095-098) supplemented with 1% non-essential amino acid (MEM Non-Essential Amino Acids Solution 10 mM 100× GIBCO 11140-050), and 10% fetal bovine serum (BIOFLUIDS DIVISION Lot No. 302030))] to 1×10$^5$ cells/mL, seeded in a 96-well clear bottom black plate (MATRIX MT4940) at 200 µL/well, and cultured.

For measurement of blank value of fluorescence for each plate, cells were not seeded in part of the wells.

JC-1 (Molecular Probes T-3168, 1 mg/mL DMSO solution) was added to a phenol red-free normal medium [MEM (GIBCO 51200-038) supplemented with 1% non-essential amino acid (MEM Non-Essential Amino Acids Solution 10 mM 100× GIBCO 11140-050), 1% L-glutamine (L-Glutamine-200 mM 100×: GIBCO 25030-149) and 10% fetal bovine serum (BIOFLUIDS DIVISION: Lot No. 302030)] at 10 µL/mL, the mixture was stirred with a vortex mixer and centrifuged at 3000 rpm for 2 min and the supernatant was filtered through a syringe filter (0.22 µm, MILLIPORE). The medium in the 96-well plate was removed and the JC-1 solution was dispensed to a cell-seeded well at 50 µL/well. A phenol red-free normal medium without JC-1 was dispensed to a blank well. The plate was placed back in a $CO_2$ incubator and incubated for 20 min.

Then, a depolarization-inducing medium containing 1 mM ouabain, 60 mM KCl, and BMS-191095 at each concentration (prepared from phenol red-free normal medium as a base) was dispensed to the well of 'test substance' by 100 µL.

BMS-191095 was dissolved in DMSO (Dimethyl Sulfoxide: SIGMA D-8779) to the final DMSO concentration of 0.1%.

A medium containing 0.1% DMSO was dispensed to the wells of 'without treatment' and 'control' by 100 µL/well. The plate was placed back in a $CO_2$ incubator and incubated.

After 2 hr, the plate was set on a fluorescence plate reader (Molecular Divices, SpectraMax GEMINI EM) heated to 37° C., and the measurement was performed under the conditions of Bottom read, Lm1 Ex: 485 nm Em: 530 nm, Lm2 Ex: 535 nm Em: 590 nm, Read/Well: 6 times. Each group contained 4 wells. The average value of fluorescence intensity of the 'blank' well was subtracted from the value of each well of 'without treatment', 'control' and 'test substance' for each of monomer fluorescence and J-aggregate fluorescence, and the ratio of each fluorescence intensity, monomer/J-aggregate, was determined.

Figure 5:
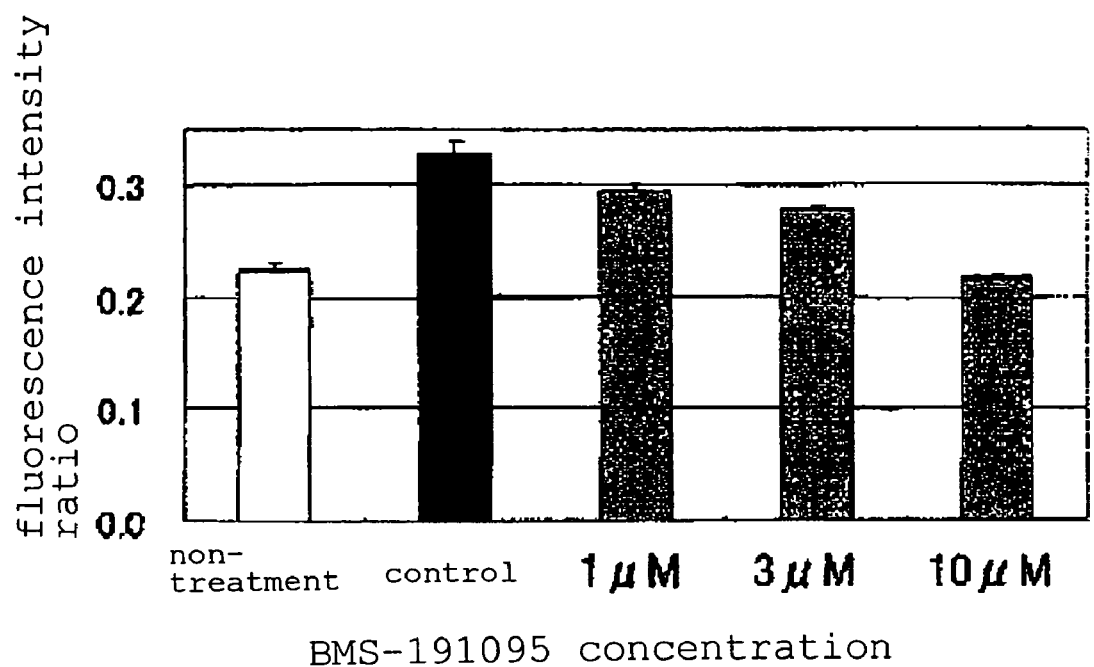
FIG. 5 shows the evaluation of the mitochondrial depolarization action of BMS-191095, wherein the concentration of BMS-191095 and difference in the fluorescence intensity ratio were used as indices (Example 2).

The results are shown in FIG. 5 (mean±standard error, N=4).

INDUSTRIAL APPLICABILITY

Using the evaluation method of the present invention, a pharmaceutical agent that selectively acts on the mitoK$_{ATP}$ channel can be evaluated. Using the evaluation method of the present invention, a pharmaceutical agent that changes the mitochondrial membrane potential can be conveniently evaluated with high precision. Using the evaluation method of the present invention, a pharmaceutical agent that changes the mitochondrial membrane potential can be evaluated in a short time.

This application is based on a patent application No. 2004-147418 filed in Japan on May 18, 2004, the contents of which are incorporated in full herein by this reference.

The invention claimed is:

1. A method of evaluating a substance, the method comprising
   (a) contacting a cultured human cell with a test substance,
   (b) contacting the cultured human cell with ouabain in the presence of 20 to 90 mM potassium ion,
   (c) measuring a change in a mitochondrial membrane potential of the cultured human cell; and
   (d) selecting a substance that changes the mitochondrial membrane potential of the cultured human cell.

2. The method of claim 1, wherein the substance in (d) inhibits cell apoptosis.

3. The method of claim 1, wherein the substance in (d) inhibits calcium influx into mitochondria.

4. The evaluation method of claim 1, wherein the substance in (d) acts on the mitochondrial ATP-sensitive K$^+$channel.

5. The method of claim 1, wherein the cultured human cell is derived from human heart, brain, nerve, liver or pancreas.

6. The method of claim 1, wherein the cultured human cell is a Girardi cell.

7. The method of claim 1, wherein the cultured human cell is cultured on a plate usable for an optical measurement method.

8. The method of claim 1, wherein ouabain is present in a concentration of 0.1 µM–3 mM.

9. The method of claim 1, wherein the change in the membrane potential is measured by the fluorescent color of a fluorescent dye incorporated into the cultured human cell.

10. The method of claim 9, wherein the fluorescent dye develops two colors.

11. The method of claim 10, wherein the change in the membrane potential is measured by the ratio of the two fluorescent colors.

12. The method of claim 9, wherein the fluorescent dye is JC-1.

* * * * *